(12) United States Patent
Park et al.

(10) Patent No.: US 9,250,168 B2
(45) Date of Patent: Feb. 2, 2016

(54) SAMPLE PRECONCENTRATOR

(75) Inventors: Han Oh Park, Daejeon (KR);
Yang-Won Lee, Daejeon (KR);
Young-Mi Koo, Gunsan-si (KR);
Kwang-Woo Jung, Daejeon (KR)

(73) Assignee: BIONEER CORPORATION (KR)

( * ) Notice: Subject to any disclaimer, the term of this patent is extended or adjusted under 35 U.S.C. 154(b) by 800 days.

(21) Appl. No.: 13/504,815

(22) PCT Filed: Mar. 31, 2010

(86) PCT No.: PCT/KR2010/001967
§ 371 (c)(1),
(2), (4) Date: Apr. 27, 2012

(87) PCT Pub. No.: WO2011/052862
PCT Pub. Date: May 5, 2011

(65) Prior Publication Data
US 2012/0216597 A1 Aug. 30, 2012

(30) Foreign Application Priority Data
Oct. 28, 2009 (KR) .................. 10-2009-0103002

(51) Int. Cl.
*G01N 1/40* (2006.01)
*G01N 35/10* (2006.01)
(52) U.S. Cl.
CPC ............ *G01N 1/405* (2013.01); *G01N 35/1097* (2013.01)
(58) Field of Classification Search
None
See application file for complete search history.

(56) References Cited

U.S. PATENT DOCUMENTS

| 7,217,311 | B2* | 5/2007 | Hong et al. ............... 75/345 |
| 7,430,928 | B2 | 10/2008 | Grate et al. |
| 8,127,595 | B2* | 3/2012 | Finlay .............. G01N 1/2214 73/23.41 |
| 2002/0127162 | A1 | 9/2002 | Smalley et al. |
| 2004/0194628 | A1 | 10/2004 | Mitra |
| 2005/0056780 | A1 | 3/2005 | Miller et al. |
| 2007/0023641 | A1 | 2/2007 | Weitz |
| 2007/0083091 | A1 | 4/2007 | Sterling et al. |
| 2008/0056946 | A1 | 3/2008 | Ahmad |

FOREIGN PATENT DOCUMENTS

| EP | 2045593 | 4/2009 |
| JP | 05256842 | 10/1993 |

(Continued)

OTHER PUBLICATIONS

Taner Yildirim et al., Metallized Nanotubes Can Absorb a Great Amount of Hydrogen, www.membrana.ru, 2005.

(Continued)

*Primary Examiner* — Robert R Raevis
(74) *Attorney, Agent, or Firm* — Cantor Colburn LLP

(57) ABSTRACT

There is provided a sample preconcentrator. The sample preconcentrator in which a sample gas injection port is coupled to a dried gas supply source and a gas analysis system to concentrate a sample gas comprises a sample concentrating unit containing an absorbent that is composed of carbon nanotube-metal nanocomplex; a conduit switching valve for selectively coupling the sample gas injection port to the dried gas supply source and the gas analysis system and controlling the absorption and desorption of the sample gas from the sample concentrating unit; and a plurality of conduits for connecting the sample gas injection port, the dried gas supply source, the gas analysis system, the sample concentrating unit and the conduit switching valve.

12 Claims, 7 Drawing Sheets

(56) References Cited

FOREIGN PATENT DOCUMENTS

| | | |
|---|---|---|
| JP | 08086778 | 4/1996 |
| KR | 1020040056132 | 6/2004 |
| KR | 1020050012556 | 2/2005 |
| KR | 1020050059364 | 6/2005 |
| KR | 100578106 | 5/2006 |
| KR | 1020060061629 | 6/2006 |

OTHER PUBLICATIONS

Lu et al., Multi-adsorbent preconcentration/focusing module for portable-GC/microsensor-array analysis of complex vapor mixtures, Analyst, 2002, pp. 1061-1068.

* cited by examiner

SAMPLE PRECONCENTRATOR

TECHNICAL FIELD

The present invention relates to sample preconcentrator which are used to absorb and desorb a gas sample, and more particularly to sample preconcentrators including an absorbent that is composed of carbon nanotube-metal nanocomplex.

BACKGROUND ART

Gas sensors have been widely used in the field of applications such as industrial safeties, environmental monitoring systems, food industries, medical services and other fields. A kind of gas sensors that senses only certain gases were mainly used in the prior art, but electronic nose technologies where gas sensors are configured in an array pattern to sense a pattern of responses to smells and odors have developed in recent years.

In order to analyze gas samples, for example, volatile organic compounds (VOCs) by using the gas above-mentioned analysis systems such as a gas sensor, an electronic nose and gas chromatography, it is necessary to require a sample preconcentrator which can absorb and desorb the gas samples.

As one example of the sample preconcentrator, Korean Patent Publication No. 10-2005-0059364 discloses a preconcentrator for absorbing and desorbing gases using an absorbent that is composed of carbon nanotubes, and a method for fabricating the same.

More particularly, the absorbent disclosed in Korean Patent Publication No. 10-2005-0059364 is formed by directly growing carbon nanotubes on electrodes. However, the preconcentrator has problems in that it is impossible to exactly measure the gas flow rate due to the pressure drop caused by the compact growth of carbon nanotubes, and it is difficult to concentrate a variety of mixed gases to a suitable concentration since the very low growth density results in small adsorption capacity of the carbon nanotubes.

As another example of the sample preconcentrator, Korean Patent Publication No. 10-2006-0061629 discloses a sample preconcentrator having the ability of removing water vapor.

The sample preconcentrator disclosed in Korean Patent Publication No. 10-2006-0061629 includes a sample concentrating unit that has the similar configuration to the most standardized type of the conventional gas absorbing/desorbing unit [see C. J. Lu and E. T. Zellers, Analyst, Vol. 127, pp 1061-1068, 2002], where a solid absorbent, for example, Tenax or Carbotrap, which has generally been used since it has the lower absorption efficiency than other absorbents but shows the low affinity to water, which leads to a decrease in the side effects caused by water moisture, has been used as the absorbent in the sample concentrating unit, and the preconcentrator is further provided with a moisture removing unit to couple a gas sensor to the rear end of the sample preconcentrator.

Here, the sample concentrating unit serves to concentrate a sample and primarily remove water moisture, and the moisture removing unit serves to secondarily remove water moisture. In order to completely remove the water moisture, the moisture removing unit uses an absorbent, for example silica beads, which can selectively absorb water as one of the polar molecules.

As another example of the sample preconcentrator, U.S. Pat. No. 7,430,928 discloses "Method and Apparatus for Concentrating Vapors for Analysis."

In the U.S. patent, the sample concentrating unit is configured by filling the inner part of porous metal foam, which is made of nickel, with an absorbent which may absorb volatile organic compounds, and fixing the metal foam and the absorbent with a wire mesh screen. Here, the porous metal foam serves to carry out the effective heat transfer of the absorbent.

However, the metal foam has a problem in that since it is very difficult to form pores of uniform size, the absorbent which the pores are filled are not uniformly distributed, and the pores which may be formed in the metal foam have a very limited pore size.

Meanwhile, in addition to the carbon nanotube and the 2,6-diphenylene oxide porous polymer-type Tenax, the volatile organic compound absorbent, which may be used, includes graphitized carbon-type Carbopack, carbon molecular sieve-type Carbosieve, Carbopack, Carboxen, etc. However, the above-mentioned absorbents have their limits in effectively concentrating a trace of volatile organic compounds.

DISCLOSURE

Technical Problem

These and other aspects of the present invention provide a sample preconcentrator using carbon nanotube-metal nanocomplex as an absorbent

Technical Solution

The sample preconcentrator according to one exemplary embodiment of the present invention is characterized in that a sample gas injection port is coupled to a dried gas supply source and a gas analysis system to concentrate a sample gas. Here, the sample preconcentrator includes a sample concentrating unit containing an absorbent that is composed of carbon nanotube-metal nanocomplex; a conduit switching valve for selectively coupling the sample gas injection port to the dried gas supply source and the gas analysis system and controlling the absorption and desorption of the sample gas from the sample concentrating unit; and a plurality of conduits for connecting the sample gas injection port, the dried gas supply source, the gas analysis system, the sample concentrating unit and the conduit switching valve.

According to one exemplary embodiment of the present invention, the sample concentrating unit may includes a first tube; carbon nanotube-metal nanocomplex filled in the first tube for absorbing and desorbing the sample gas; a fixing member arranged in both ends of the carbon nanotube-metal nanocomplex to fix the carbon nanotube-metal nanocomplex; and a heating member for heating the first tube to desorb the volatile organic compounds absorbed into the carbon nanotube-metal nanocomplex.

The carbon nanotube-metal nanocomplex may have a size of 10 nm to 1,000 nm, and the carbon nanotube-metal nanocomplex may be present at an amount of 1 mg to 1 g.

The fixing member may include a pair of glass wools each having both ends arranged respectively in the ends of the carbon nanotube-metal nanocomplex; and a pair of stainless steel meshes arranged respectively in the outer sides of the glass wools.

The heating member may be made of a nickel-chromium (Ni—Cr) or platinum wire and may include a hot wire surrounding the first tube.

The sample concentrating unit may further include a temperature sensor for sensing the temperature of the first tube and an insulating tube installed inside the temperature sensor.

The sample preconcentrator according to one exemplary embodiment of the present invention may further include a constant temperature unit for preventing the condensation of the sample gas. In this case, the constant temperature unit may include a constant temperature block and a constant temperature tube.

The conduit switching valve may be composed of 10-port valves, and the back-flush functions may be carried out using the conduit switching valve.

The sample preconcentrator according to one exemplary embodiment of the present invention may further include a pressure sensor for sensing the pressure of a dried gas supplied from the dried gas supply source; a moisture removing unit for removing water moisture present in the dried gas; a flow rate controller for controlling the flow rate of the dried gas; and a pump for discharging the dried gas passed through the sample concentrating unit.

Advantageous Effects

The sample preconcentrator as configured above is operable at a lower desorption temperature than that of the conventional sample preconcentrators due to the quick and effective thermal conductivity since the sample preconcentrator uses an absorbent that is composed of carbon nanotube-metal nanocomplex. Also, the sample preconcentrator may be useful to effectively concentrate the noxious gas samples such as volatile organic compounds.

Also, since the excellent thermal diffusion by the carbon nanotube-metal nanocomplex is carried out in the step of supplying the desorbed gas sample to the gas analysis system, a sample of the desorbed volatile organic compounds may be effectively focused to have the excellent decomposable ability.

In addition, the sample preconcentrator may be useful to reduce the difference in the desorption temperature of the volatile organic compounds to be desorbed and improve the decomposable ability of the gas analysis system since the hot wire is made of a nickel-chromium or platinum wire to heat the sample concentrating unit within a short time period of 5 seconds.

Additionally, the sample preconcentrator may be useful to carry out the back-flush function by supplying the desorbed volatile organic compounds to the gas analysis system and simultaneously operating the conduit switching valve.

Furthermore, the sample preconcentrator may be useful to prevent the volatile organic compounds from being condensed in the drift conduit and the conduit switching valve by using the constant temperature unit.

DESCRIPTION OF DRAWINGS

FIG. 1 shows the configuration of the sample preconcentrator in the step of absorbing a sample, and FIG. 2 shows the configuration of the sample preconcentrator in the step of desorbing a sample.

FIG. 3 shows a cross-sectional view in a longitudinal direction of the sample concentrating unit 110, and FIG. 4 shows a cross-sectional view taken from line "IV-IV" as shown in FIG. 3.

BEST MODE

Figure 1:
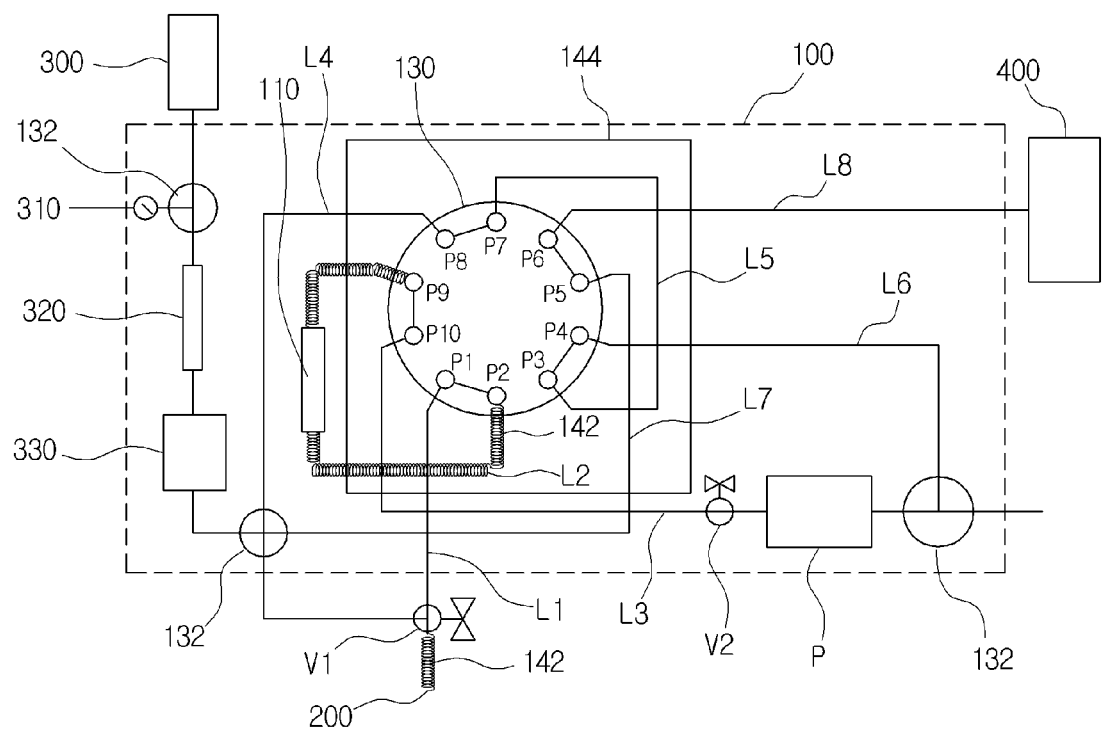
FIGS. 1 and 2 are schematic diagrams illustrating the configurations of a sample preconcentrator according to one exemplary embodiment of the present invention. Here.

Hereinafter, the sample preconcentrator according to the exemplary embodiments of the present invention will be described in detail referring to the accompanying drawings. Also, it is considered that parts that have the same or substantially identical functions and effects in the accompanying drawings have the same reference numerals. For the detailed description of the present invention, it is however considered that descriptions of known components and their related configurations according to the exemplary embodiments of the present invention may be omitted since they are judged to make the gist of the present invention unnecessarily confusing. Therefore, it should be considered that some of the features shown in the drawings may be curtailed or simplified for the convenience' sake and the drawings and their components are not necessarily shown at a suitable ratio. However, it should be understood that other equivalents and modifications could be made thereto, as apparent to those skilled in the art.

Figure 2:
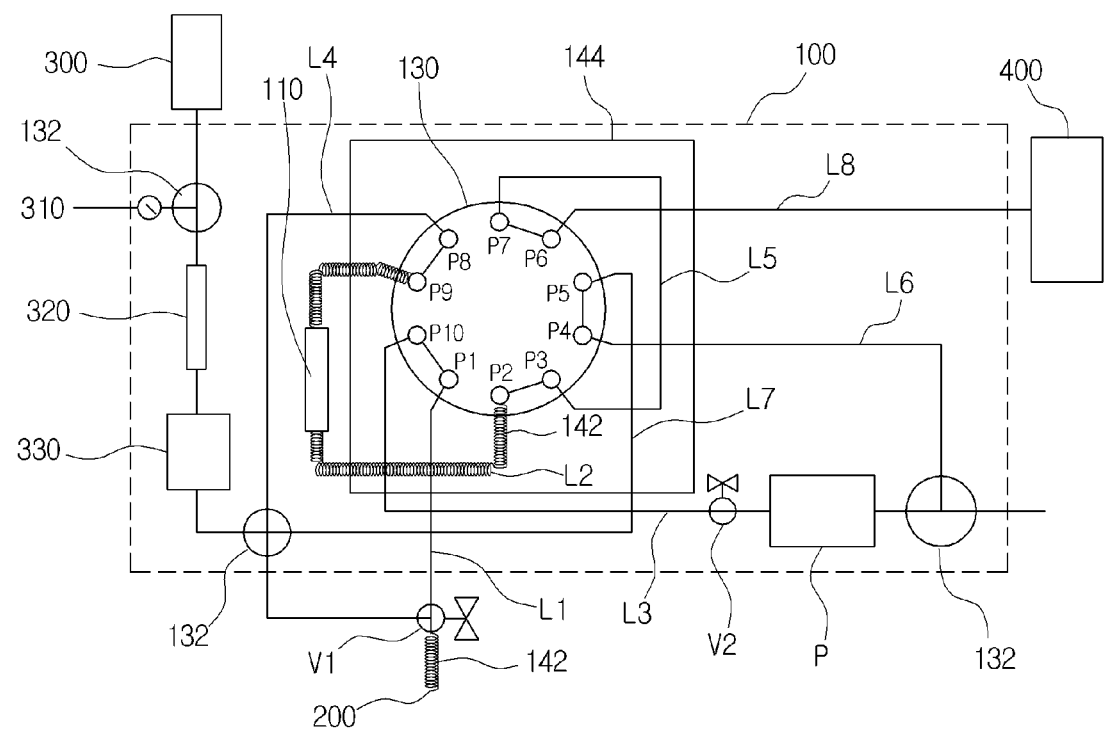

FIGS. 1 and 2 are schematic diagrams illustrating the configurations of a sample preconcentrator according to one exemplary embodiment of the present invention. Here, FIG. 1 shows the configuration of the sample preconcentrator in the step of absorbing a sample, and FIG. 2 shows the configuration of the sample preconcentrator in the step of desorbing a sample.

Figure 3:
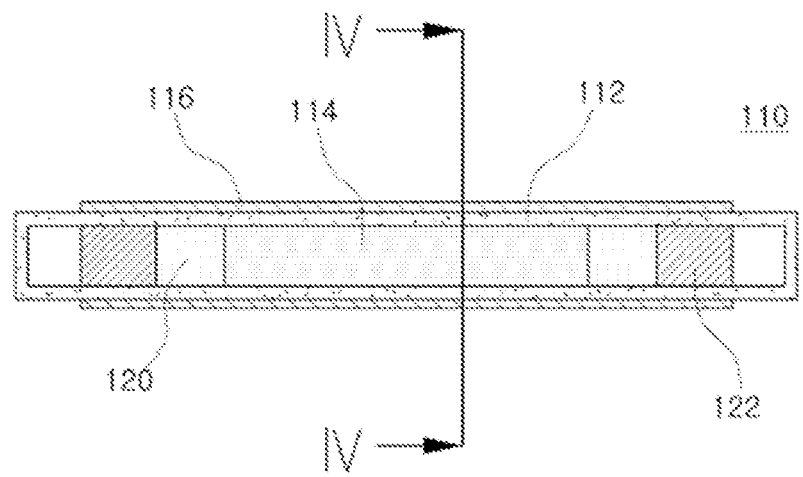
FIGS. 3 and 4 are schematic diagrams illustrating the configurations of a sample concentrating unit 110 according to one exemplary embodiment of the present invention. Here.
Figure 4:
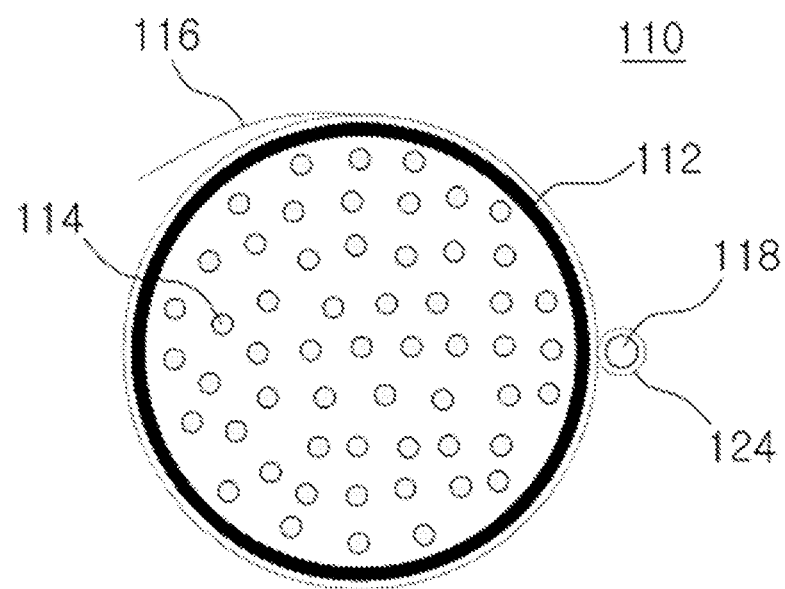

Also, FIGS. 3 and 4 are schematic diagrams illustrating the configurations of a sample concentrating unit according to one exemplary embodiment of the present invention. Here, FIG. 3 shows a cross-sectional view in a longitudinal direction of the sample concentrating unit, and FIG. 4 shows a cross-sectional view taken from line "IV-IV" as shown in FIG. 3.

The sample preconcentrator 100 in which a sample gas injection port 200 is coupled to a dried gas supply source 300 and a gas analysis system 400 according to one exemplary embodiment of the present invention includes a sample concentrating unit 110, a conduit switching valve 130 and a plurality of conduits.

The sample gas injection port 200 serves to supply sample gases in the atmosphere to the sample concentrating unit 110 of the sample preconcentrator 100.

The dried gas supply source 300 serves to supply the dried gas, for example nitrogen gas to the sample concentrating unit 110, and the gas analysis system 400 serves to analyze samples, for example volatile organic compounds, which is absorbed into the sample concentrating unit 110 and desorbed from the sample concentrating unit 110.

The sample concentrating unit 110 includes a heat-resistant glass tube 112, carbon nanotube-metal nanocomplex 114, a hot wire 116, a temperature sensor 118 and fixing members 120 and 122.

The carbon nanotube-metal nanocomplex 114 functioning as an absorbent is filled inside the glass tube 112, and a glass wool 120 and a stainless steel mesh 122 are arranged in both ends of the glass tube 112, respectively, to fix the carbon nanotube-metal nanocomplex 114. In this case, the stainless steel meshes 122 are arranged in the outer sides of the glass wools 120, respectively.

The glass tube 112 is a heat-resistant glass that is physically and chemically stable at a temperature of 500° C. or above, and is made of materials that can swiftly transfer a sufficient amount of heat to the absorbent.

A hot wire 116 is installed outside the glass tube 112, and the hot wire 116 is used to increase the temperature of the glass tube 112 when the concentrated sample, for example a volatile organic compound is desorbed from the carbon nanotube-metal nanocomplex 114 with which the glass tube 112 is filled.

The hot wire 116 is made of a nickel-chromium (Ni—Cr) or platinum (Pt) wire having a resistance of 5Ω to 10Ω in order to facilitate an increase in the temperature of the glass tube 112 to 350° C. within a short time period of 5 seconds.

The temperature sensor 118 is installed inside the insulating tube 124 in order to rapidly sense the changes in the temperature of the glass tube 112 as the temperature of the glass tube 112 increases. In this case, the insulating tube 124 may be made of insulating materials such as micropipet capillary, heat-resistant capillary glass tubes or polyimides.

Meanwhile, in case the sample concentrating unit 110 is provided with a system for allowing a suitable amount of electric current to flow to the hot wire 116 at a temperature that is set by a hardware program (not shown) for the purpose of the control of the sample preconcentrator 100, it is possible to omit the temperature sensor 118 for clarity.

The compounds disclosed in U.S. Pat. No. 7,217,311 (Method of Producing Metal Nanocomposite Powder Reinforced with Carbon Nanotubes and the Powder Prepared Thereby) and Korean Patent Publication No. 10-2005-0012556 (Metal Nanocomposite Powders Reinforced with CarbonNanotubes and Their Fabrication Process) may be used as the carbon nanotube-metal nanocomplex 114 that are used as the absorbent for the volatile organic compounds.

The carbon nanotube-metal nanocomplex 114 have metal nanoparticles in the form of powder particles uniformly distributed in the carbon nanotubes. In this case, the metal nanoparticles have predetermined sizes, but the nanoparticles are coupled to each other to have a round shape. Therefore, the carbon nanotube-metal nanocomplex 114 have a wide surface area and show their uniform and excellent thermal conductivity.

When the above-mentioned carbon nanotube-metal nanocomplex 114 are used as the absorbent, the sample preconcentrator is configured to effectively concentrate the noxious gas samples such as volatile organic compounds, and also may be operable at a lower desorption temperature than that of the conventional sample preconcentrators due to the quick and effective thermal conductivity of the carbon nanotube-metal nanocomplex 114. Here, the conventional sample preconcentrators are operated by using the thermal absorption and desorption method.

Furthermore, since the excellent thermal diffusion by the carbon nanotube-metal nanocomplex 114 is carried out in the step of supplying the desorbed gas sample to the gas analysis system 400, a sample of the desorbed volatile organic compounds may be effectively focused to have the excellent decomposable ability.

The metals in the carbon nanotube-metal nanocomplex 114 may be most of metal materials, which are used to form aqueous metal salts or metal hydrates, or oxides thereof. For example, the metal may be selected from the group consisting of cobalt, copper, nickel, titanium, silver, aluminum, iron, tungsten, oxides of cobalt, oxides of copper, oxides of nickel, oxides of titanium, or oxides of silver, oxides of aluminum, oxides of iron, oxides of tungsten, and the like. The metal may be included at an amount of 10% to 95%, based on the total amount of the carbon nanotube.

The size of the carbon nanotube-metal nanocomplex 114 may be in a range of 10 nm to 1,000 nm, and the carbon nanotube-metal nanocomplex 114 may be present at an amount of 1 mg to 1 g.

The conduit switching valve 130 is configured to couple the sample gas injection port 200 to the sample concentrating unit 110 so that the sample concentrating unit 110 can absorb the sample gases, and also to connect the gas analysis system 400 to the sample concentrating unit 110 so that the sample (volatile organic compounds) desorbed from the sample concentrating unit 110 can be supplied to the gas analysis system 400.

As described above, the conduit switching valve 130 is configured to selectively combine the sample gas injection port 200, the dried gas supply source 300 and the gas analysis system 400 with the sample concentrating unit 110. Hereinafter, the coupling relations of their components will be described in detail.

According to one exemplary embodiment of the present invention, the conduit switching valve 130 is composed of 10-port valves each having 10 ports. Here, the 10 ports are represented by reference numerals P1 to P10, and a pair of ports among the 10 ports are connected with each other by means of inner conduits.

For example, the first port (P1) is connected with the second port (P2) by means of the inner conduits, and the third port (P3) is connected with the fourth port (P4) by means of the inner conduits. In the same manner, the fifth port (P5) is connected with the sixth port (P6), the seventh port (P7) is connected with the eighth port (P8), and the ninth port (P9) is connected with the tenth port (P10).

Referring to FIG. 1, the first port (P1) is connected with the sample gas injection port 200 via the first conduit (L1). A 2-way valve (V1) is installed in the first conduit (L1) to selectively supply a sample gas to the first port (P1).

The second port (P2) connected with the first port (P1) via the inner conduit is connected with the ninth port (P9) through the second conduit (L2), and the sample concentrating unit 110 is installed in the middle of the second conduit (L2).

The third conduit (L3) is connected with the tenth port (P10) connected with the ninth port (P9) via the inner conduit, and a 2-way valve (V2) and a pump (P) are sequentially installed in the third conduit (L3).

The fourth conduit (L4) is divided in a position of installing the 2-way valve (V1) of the first conduit (L1), and is then connected with the eighth port (P8), and the seventh port (P7) connected with the eighth port (P8) via the inner conduit is connected with the third port (P3) through the fifth conduit (L5), and the fourth port (P4) connected with the third port (P3) via the inner conduit is connected with the third conduit (L3) in the rear of the pump (P) via the sixth conduit (L6).

Meanwhile, the fourth conduit (L4) communicates midway with the seventh conduit (L7) through which the dried gas supply source 300 is connected with the fifth port (P5), and the sixth port (P6) connected with the fifth port (P5) via the inner conduit is connected with the gas analysis system 400 through the eighth conduit (L8). Here, a part represented by reference numeral 132 represents a part with which at least 2 conduits communicate. In this case, the part represented by reference numeral 132 seems to be crossed in the drawings, but does not in fact communicate with each other.

Meanwhile, only in the front of the seventh conduit (L7) through which the dried gas supply source 300 is connected with the fifth port (P5) are installed a pressure sensor 310 for sensing the pressure of the dried gas, a moisture removing unit 320 for removing water moisture present in the dried gas and a flow rate controller 330 for controlling a flow rate of the dried gas.

Also, some of the conduits are surrounded by the constant temperature tube 142, and the conduit switching valve 130 and some of the conduits are arranged inside the constant temperature block 144.

Hereinafter, the steps of absorbing and desorbing a sample will be described in detail with reference to FIGS. 1 and 2.

The step of absorbing a sample to concentrate volatile organic compounds which are present at a very small amount in the atmosphere is now described in detail with reference to FIG. 1. Here, the ports (P1 to P10) in the conduit switching valve 130 are connected, respectively to the corresponding conduits, as described above.

In this circumstance, when the air containing volatile organic compounds is inhaled through the sample gas injection port 200, the air is sequentially passed through the first conduit (L1), the first port (P1) and the second port (P2), the second conduit (L2), the ninth port (P9) and the tenth port (P10), and the third conduit (L3), and finally exhausted to the outer environment. In this case, the volatile organic compounds are absorbed into the carbon nanotube-metal nanocomplex 114 in the sample concentrating unit 110 in the course of the air flow.

Meanwhile, the dried gas supply source 300 supplies the dried gas, for example high-purity nitrogen in the step of absorbing a sample. The pressure and flow rate of the supplied nitrogen are controlled by the pressure sensor 310 and the flow rate controller 330, respectively, so that the supplied nitrogen can be supplied to the gas analysis system 400, and the water moisture in the nitrogen gas is removed in the moisture removing unit 320, for example a moisture trap.

Hereinafter, the step of desorbing a sample to analyze the volatile organic compound absorbed according to the above-mentioned step will be described in detail with reference to FIG. 2.

First of all, the conduit switching valve 130 is operated to desorb the sample absorbed into the carbon nanotube-metal nanocomplex 114. After the operation of the conduit switching valve 130, when the conduit switching valve 130 turns counterclockwise at an angle approximately 30° from the configuration as shown in FIG. 1, the conduit switching valve 130 returns to the configuration as shown in FIG. 2.

Therefore, the first conduit (L1) is connected with the tenth port (P10), the second conduit (L2) is connected with the first port (P1) and the eighth port (P8), and the third conduit (L3) is connected with the ninth port (P9). Also, the fourth conduit (L4) is connected with the seventh port (P7), the fifth conduit (L5) is connected with the second port (P2) and the sixth port (P6), and the sixth conduit (L6) is connected with the third port (P3). In addition, the seventh conduit (L7) is connected with the fourth port (P4), and the eighth conduit (L8) is connected with the fifth port (P5).

When the conduit switching valve 130 is operated as described above, the hot wire 116 operates at the same time as the operation of the valve 130, or right after the operation of the valve 130. Therefore, the temperature of the glass tube 112 in the sample concentrating unit 110 increases to approximately 350° C. within 5 seconds after the operation of the hot wire 116.

As the temperature of the glass tube 112 increases, the volatile organic compounds desorbed from the carbon nanotube-metal nanocomplex 114 are supplied to the gas analysis system 400 via the second conduit (L2), the first port (P1) and the second port (P2), the fifth conduit (L5), the sixth port (P6) and the fifth port (P5), and the eighth conduit (L8).

When the desorption of the sample is completed, the conduit switching valve 130 returns to an original position, that is, a position as shown in FIG. 1, to perform a back-flush mode.

This enables completely separating the desorption step from the step of injecting the desorbed sample injected into the gas sensor and the gas analysis system 400 and flushing the fifth conduit (L5) as well.

The above-mentioned conduits (L1 to L8) may use a variety of tubes which are made of stainless steel, Teflon and Tygon, depending on the temperature and function of the flowing gas or the connected conduits, and when a gas chromatography is connected with the rear end of the eighth conduit (L8), the eighth conduit (L8) may be used through the connection of the capillary separation column with the eighth conduit (L8).

Also, the washing of the sample concentrating unit 110 is carried out by operating only the 2-way valve (V2) and the pump (P) when the conduit switching valve 130 is changed into a position as shown in FIG. 1, followed by increasing the temperature of the glass tube 112 to desorb and discharge the volatile organic compounds remaining in the carbon nanotube-metal nanocomplex 114.

FIGS. 5 to 8 show specific experimental examples illustrating the properties of absorbing and desorbing the carbon nanotube-metal nanocomplex 114, and of concentrating the volatile organic compounds.

Experimental Example 1

In order to determine how rapidly the volatile organic compounds are desorbed from the carbon nanotube-metal nanocomplex 114 and injected into the gas analysis system 400 when instantly heating the sample concentrating unit 110, a desorption bandwidth was measured.

This experiment was carried out by injecting volatile organic compounds into the sample preconcentrator 100, and operating the conduit switching valve 130 while instantly increasing the temperature of the volatile organic compounds, thereby measuring the full widths at half maximum (FWHM) of the volatile organic compounds which were sensed by a flame ionization detector (FID) of the conventional gas chromatography (7890A from Agilent).

In this case, the conventional absorbent (Carbopack X) and various kinds of carbon nanotube-metal nanocomplex 114 (all the products from "BIONEER Corp": 10 mg of CNT-Co having a particle size of 1,000 nm, 10 mg of CNT-Ni having a particle size of 100 nm, and 10 mg of CNT-Cu having a particle size of 1,000 nm) were used as the absorbent, and isopropyl alcohol, 2-butanone, 1,2-dichloroethane, benzene, toluene, ethylbenzene, p-xylene and o-xylene were used as the volatile organic compounds (VOCs). In this case, a concentration of the volatile organic compounds was adjusted to 50 ppb.

Figure 5:
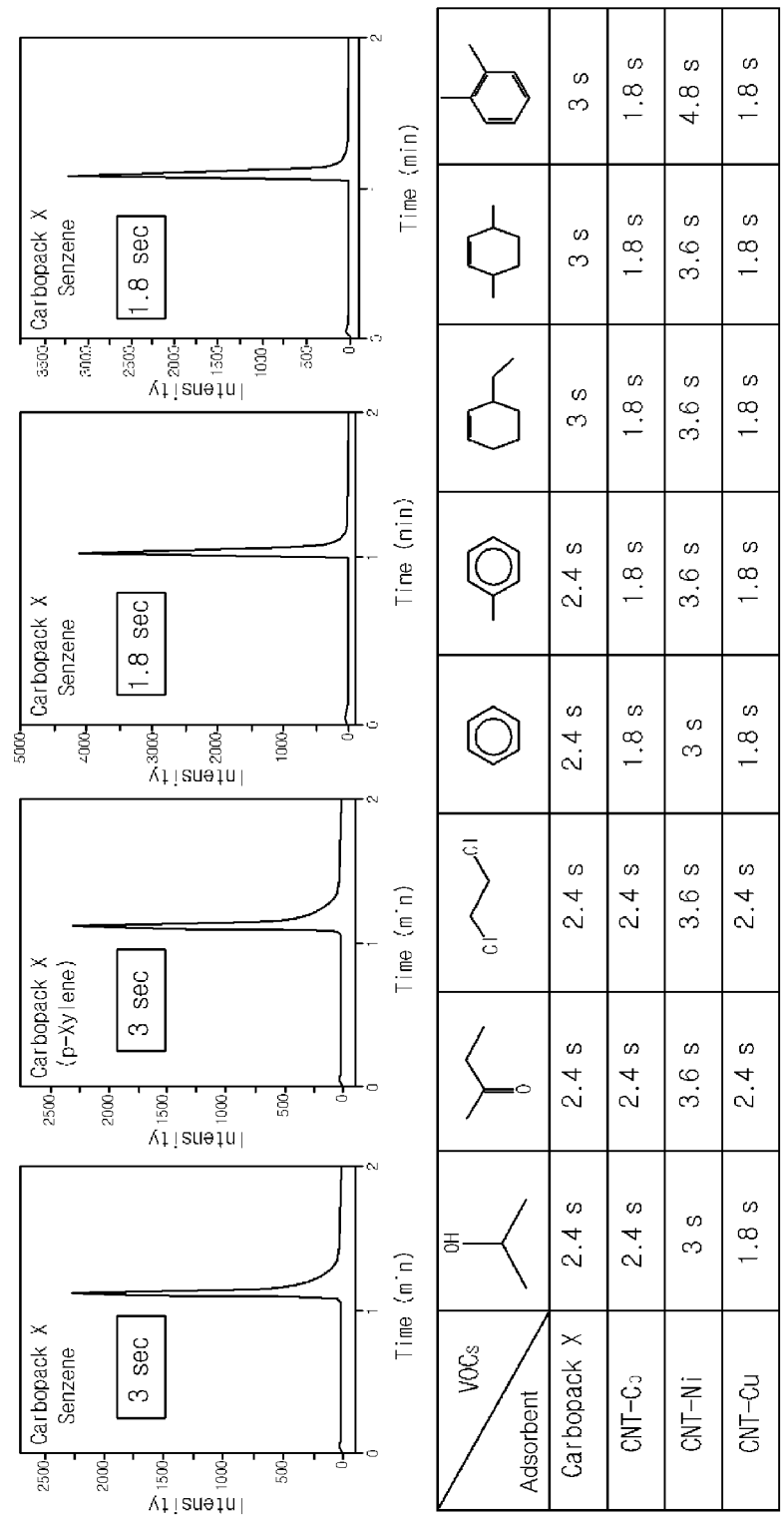
FIG. 5 is a diagram illustrating a graph and a table including the results obtained by measuring the ability of desorbing volatile organic compounds from the carbon nanotube-metal nanocomplex 114 which are used as an absorbent in the sample concentrating unit 110 according to one exemplary embodiment of the present invention.

The results obtained by measuring the abilities of the carbon nanotube-metal nanocomplex 114 to desorb the organic compounds are listed in the graph and table as shown in FIG. 5.

As shown in FIG. 5, it was revealed that the CNT-Ni nanoparticles in the carbon nanotube-metal nanocomplex 114 have a particle size of 100 nm, which is highly lower than the particle size (i.e., 1,000 nm) of the CNT-Co and CNT-Cu nanoparticles. Therefore, the desorption of the organic compounds is affected by the size of the carbon nanotube-metal nanocomplex 114.

However, when the different kinds of the metal nanoparticles having the same particle size were used, the FWHMs of the metal nanoparticles were observed within 3 seconds, and have similar results. Therefore, it was seen that the absorbed volatile organic compounds are effectively desorbed from the carbon nanotube-metal nanocomplex 114 at a room temperature.

Exemplary Embodiment 2

This experiment was carried out to measure an absorption volume (i.e., breakthrough volume) to the carbon nanotube-metal nanocomplex 114.

The absorption volume is defined as a volume of an atmospheric sample that is inhaled until a concentration of a certain sample after passing through the sample concentrating unit 110 is reduced to 10% of the concentration of the sample before passing through the sample concentrating unit 110.

This experiment was carried out in the following procedures. First, a 250 ml sampling loop was installed instead of the sample preconcentrator 100 to sample a certain concentration of the gas mixture, and analyzed using the capillary separation column (HP-1, 30 m×0.32 mm×1 μm) of the gas chromatography and the FID detector.

Next, the sample preconcentrator 100 of the present invention was installed in the front end of the 250 μl sampling loop, and the volatile organic compounds was inhaled at a constant rate of 100 ml/min without carrying out the desorption step of the sample concentrating unit 110, and then analyzed using the gas chromatography.

The gas mixture was repeatedly injected at a rate of 100 ml/min until the carbon nanotube-metal nanocomplex 114 in the sample concentrating unit 110 is saturated. Then, if the peak intensity of the analytical sample is measured to be 10% of the peak intensity as measured in the 250 μl sampling loop, the volume of the inhaled gas mixture was determined as the absorption volume.

The absorptions of 500 ppb of the volatile organic compounds (for example, benzene, toluene, ethylbenzene, p-xylene, o-xylene 2-propanol, 2-butanone, 1,2-dichloroethane) to the various kinds of carbon nanotube-metal nanocomplex (all the products from "BIONEER Corp": 10 mg of CNT-Al having a particle size of 500 nm, CNT-Cu having a particle size of 1,000 nm, and CNT-Ni having a particle size of 100 nm) were measured. Then, the experimental results are shown in FIGS. 6 to 8.

Figure 6:
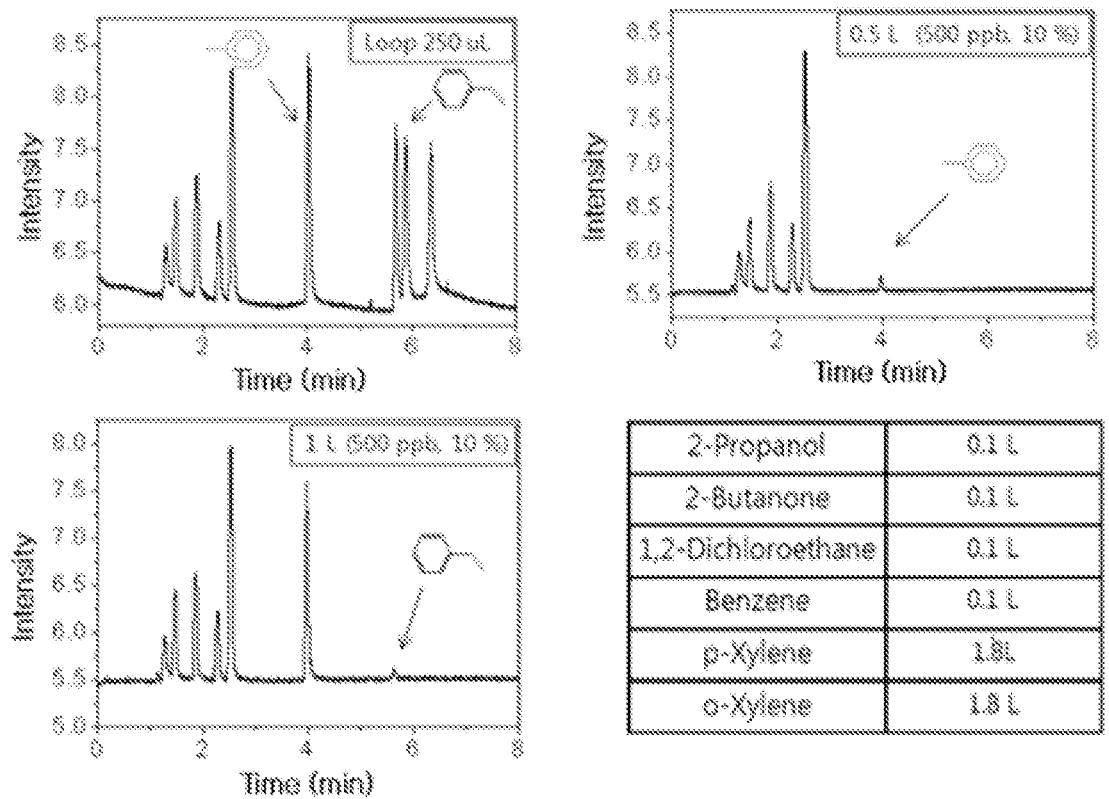
FIGS. 6 to 8 are diagrams illustrating graphs and tables including the results obtained by measuring the ability of absorbing volatile organic compounds into the carbon nanotube-metal nanocomplex 114 which are used as an absorbent in the sample concentrating unit 110 according to one exemplary embodiment of the present invention.
Figure 7:
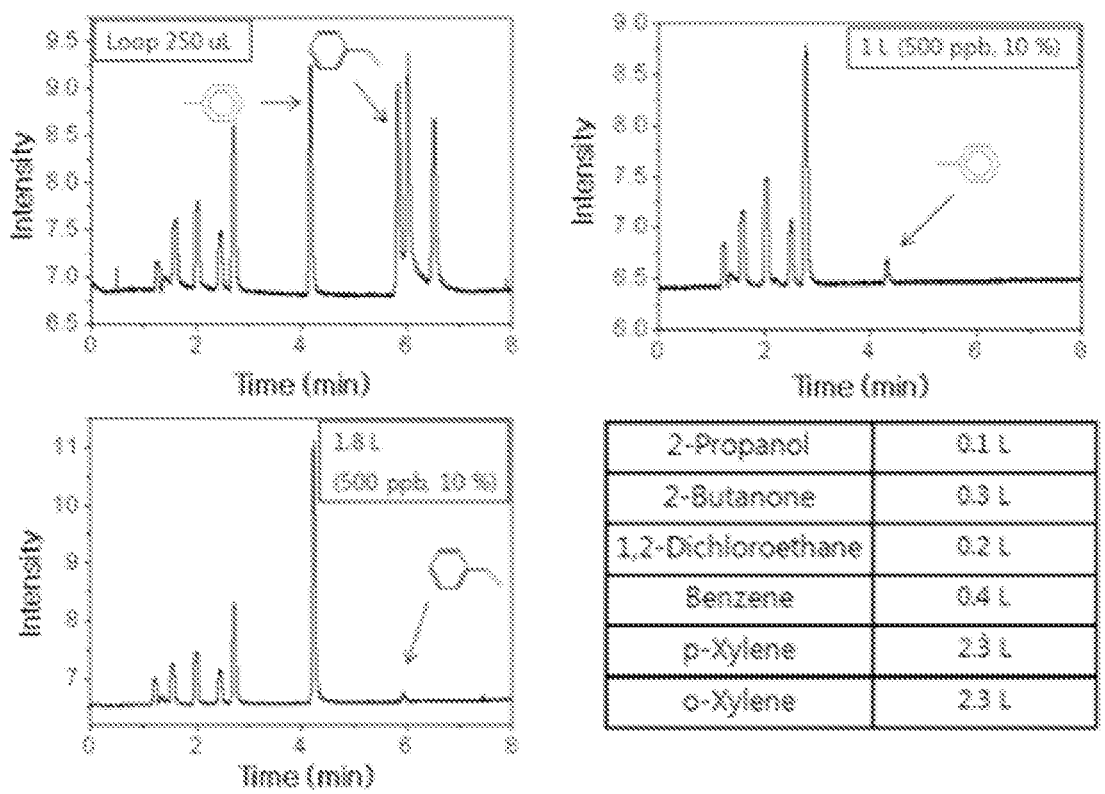
Figure 8:
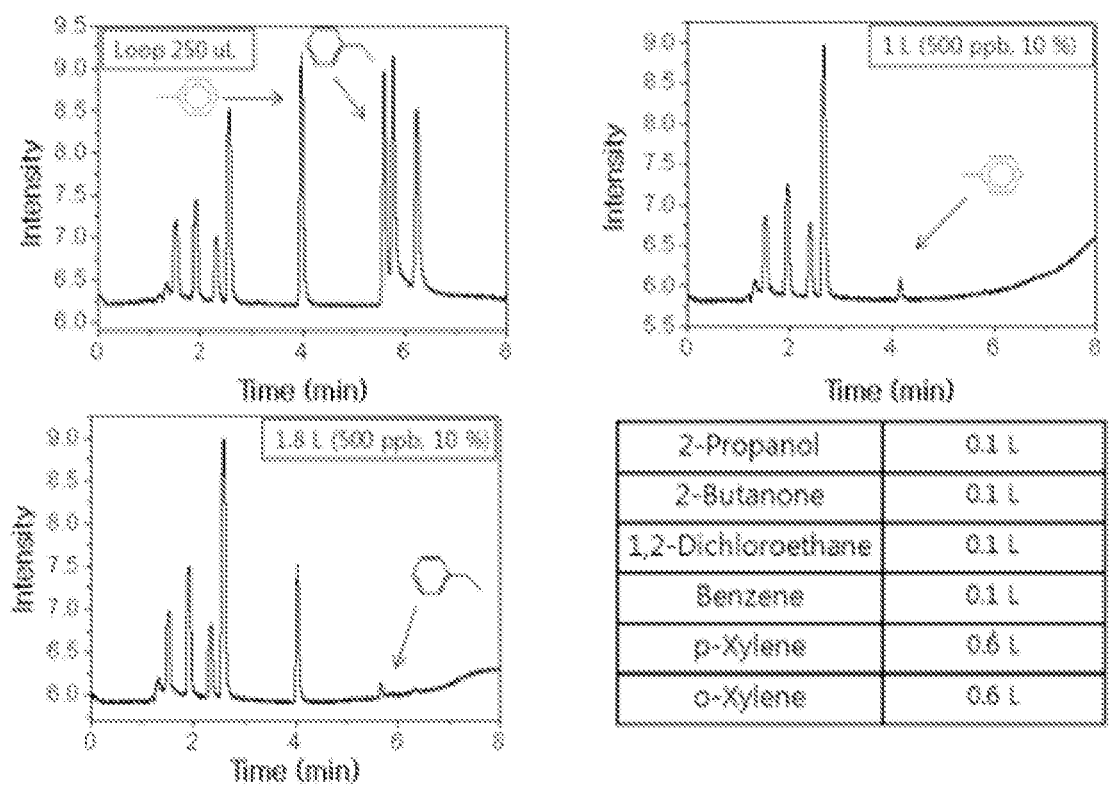

In FIGS. 6 to 8, FIG. 6 shows that 10 mg of CNT-Al having a particle size of 500 nm was used as the absorbent, FIG. 7 shows that CNT-Cu having a particle size of 1,000 nm was used as the absorbent, and FIG. 8 shows that CNT-Ni having a particle size of 100 nm was used as the absorbent.

According to the this experimental results, it was revealed that there is the difference in the performances of the carbon nanotube-metal nanocomplex 114 according to the size of the metals and metal nanoparticles coupled to the carbon nanotube-metal nanocomplex 114, but the carbon nanotube-metal nanocomplex 114 may be used to effectively concentrate the volatile organic compounds having a higher molecular weight than benzene, when compared to the conventional absorbents. Also, it was confirmed that the carbon nanotube-metal nanocomplex 114 have a more excellent desorption performance than the conventional absorbents.

Therefore, the sample preconcentrator 100 including the absorbent according to the present invention may be useful to effectively improve the decomposable ability of the gas sensor or the gas analysis system 400.

As described above, the sample preconcentrator 100 according to the present invention may be used to develop portable analytical devices to detect, classify and monitor a trace (several ppb) of volatile organic compounds. Also, the sample preconcentrator 100 may be used to supervise the residential and industrial environments such as volatile components in the atmosphere, volatile components in the biological species, aromatic components in the detergents, hydrocarbons in the diesel filter papers, and bad smells in a real-time manner, and may play an important role in the development of next-generation hypersensitive sensors that can be used for chemistry, medical sciences, military affairs and national security.

The invention claimed is:

1. A sample preconcentrator comprising;
   a carbon nanotube-metal nanocomplex for absorbing and desorbing a sample gas;
   a sample concentrating unit including the carbon nanotube-metal nanocomplex;
   a sample gas injection port, a dried gas supply source, and a gas analysis system connected to the sample preconcentrator; and
   a conduit switching valve for selectively coupling the sample gas injection port, the dried gas supply source and the gas analysis system with the sample concentrating unit and controlling the absorption and desorption of the sample gas from the sample concentrating unit.

2. The sample preconcentrator according to claim 1, wherein the sample concentrating unit comprises:
   a first tube;
   carbon nanotube-metal nanocomplex filled in the first tube for absorbing and desorbing the sample gas;
   a fixing member arranged in both ends of the carbon nanotube-metal nanocomplex to fix the carbon nanotube-metal nanocomplex; and
   a heating member for heating the first tube in order to desorb volatile organic compounds absorbed into the carbon nanotube-metal nanocomplex.

3. The sample preconcentrator according to claim 2, wherein the carbon nanotube-metal nanocomplex has a size of 10 nm to 1,000 nm.

4. The sample preconcentrator according to claim 2, wherein the carbon nanotube-metal nanocomplex are present at an amount of 1 mg to 1 g.

5. The sample preconcentrator according to claim 2, wherein the fixing member comprises:
   a pair of glass wools each having both ends arranged respectively in both ends of the carbon nanotube-metal nanocomplex; and
   a pair of stainless steel meshes arranged respectively in the outer sides of the glass wools.

6. The sample preconcentrator according to claim 2, wherein the heating member is made of a nickel-chromium (Ni—Cr) or platinum wire and comprises a hot wire surrounding the first tube.

7. The sample preconcentrator according to claim 2, wherein the sample concentrating unit further comprises an insulating tube and a temperature sensor installed inside the insulating tube for sensing the temperature of the first tube.

8. The sample preconcentrator according to claim 2, further comprising a constant temperature unit for preventing the condensation of the sample gas.

9. The sample preconcentrator according to claim 8, wherein the constant temperature unit comprises a constant temperature block and a constant temperature tube.

10. The sample preconcentrator according to claim 1, wherein the conduit switching valve is composed of 10-port valves.

11. The sample preconcentrator according to claim 10, wherein the conduit switching valve is used to carry out the back-flush functions.

12. The sample preconcentrator according to claim 1, wherein the dried gas supply source comprises:
   a pressure sensor for sensing the pressure of a dried gas supplied from the dried gas supply source;
   a moisture removing unit for removing water moisture present in the dried gas;
   a flow rate controller for controlling the flow rate of the dried gas; and
   a pump for discharging the dried gas passed through the sample concentrating unit.

* * * * *